United States Patent [19]
Lehmussaari et al.

[11] Patent Number: 5,767,143
[45] Date of Patent: Jun. 16, 1998

[54] OPHTHALMOLOGICAL PREPARATION

[75] Inventors: Kari Lehmussaari; Olli Oksala; Timo Reunamaki, all of Tampere, Finland

[73] Assignee: Santen OY, Niittyhaankatu, Finland

[21] Appl. No.: 542,714

[22] Filed: Oct. 13, 1995

Related U.S. Application Data

[63] Continuation of Ser. No. 232,075, filed as PCT/FI93/00326, Aug. 18, 1993, abandoned.

[30] Foreign Application Priority Data

Aug. 20, 1992 [SE] Sweden ................................. 9202398

[51] Int. Cl.⁶ .................................................. A61K 31/415
[52] U.S. Cl. ............................................. 514/397; 514/912
[58] Field of Search ................................ 514/397, 912

[56] References Cited

FOREIGN PATENT DOCUMENTS

| 0 253 717 | 1/1988 | European Pat. Off. |
| WO 91/19481 | 12/1991 | WIPO . |
| WO9119481 | 12/1991 | WIPO . |

*Primary Examiner*—Zohreh Fay

[57] ABSTRACT

The present invention relates to an eye drop formulation, which, in combination, comprises a single polymer, pilocarpine, a beta-blocking agent and an ophthalmologically acceptable carrier wherein the pH of the formulation is from 3.5 to 5.8 and the viscosity is from 10 to 25000 mPas.

11 Claims, No Drawings

OPHTHALMOLOGICAL PREPARATION

This application is a continuation of application Ser. No. 08/232,075, filed Apr. 26, 1994, now abandoned which is a 379 of the PCT/FI93/00326 filed Aug. 18, 1993.

The object of the present invention is an ophthalmological preparation, specifically an eye drop formulation, which, in combination, comprises pilocarpine and a further agent for the treatment of ocular hypertension, such as a β-blocking agent, e.g. timolol, as well as an ophthalmologically acceptable carrier and optionally further, ophthalmologically acceptable adjuvants. The invention further concerns a process for the preparation of the said formulation, as well as the use thereof for the treatment of intraocular hypertension and glaucoma.

From the EP-patent application 253 717 it is known to administer into the eye simultaneously a β-blocker and pilocarpine in the form of an eye drop combination formulation which is buffered to a pH of 6.0 to 6.8. The use of a combination formulation rather than administering the two drugs separately has, in addition to beneficial therapeutical effects, also the further advantage of improving patient compliance.

However, the formulation according to the EP-patent application 253 717 has the disadvantage that the solution formed remains usable only for a short period of time, wherefore it has to be made shortly before first use, either by combining a solid substance and a solution, or two separate solutions. Thus the formulation according to this EP-patent application cannot be packed and delivered to the user in the traditional bottle package or as a unit-dose package, as both package forms require that the solution contained therein is ready for administration into the eye, and also that it is sufficiently stable.

The formulation disclosed in the EP-patent 253 717 places strict demands on the packaging technology used, and also on patient acceptance. Further, the highly complicated packages are substantially more expensive than the traditional ones because they have to be constructed so as to allow the preparation to be prepared shortly before administration. The different components of the formulation are combined by somebody else than the manufacturer and thus there is a definite risk for dosage mistakes. In order to ensure sterility also after mixing of the components, the formulation contains antimicrobial preservatives.

However, it has for a long time been known that antimicrobial preservatives exhibit a number of side effects on the cornea. In eye therapy, preservative-free formulations, packaged in unit-dose form, thus gain increasingly more use. Another reason for abandoning multi-dose containers is that, especially in hospital use, the same container is used for administering drug to several patients, which increases the risk for contamination of the drug and the spreading of contagious diseases by means of the eye drop solution.

According to the invention we have now surprisingly discovered that it is possible to make a combination eye drop formulation, which in the same solution contains pilocarpine and a further agent for the treatment of ocular hypertension, especially a β-blocker, and which is sufficiently stable to be packaged and delivered in ready-to-use-form in traditional eye drop bottles or in unit-dose containers.

This is achieved according to the invention by providing a formulation which has a pH of between 3.5 and 5.8, and a viscosity of 10 to 25000 mPas.

Preferably the pH is from 4.5 to 5.5 and the viscosity not more than 150 mPas, espcially 15 to 50 mPas.

The viscosity is measured with a Brookfield-viscosimeter (type LVDV-III) at a temperature of 22° C., and a shear rate (D) of 1 s$^{-1}$ for viscosities in the range of 100 to 25000 mPas, and a shear rate of 8 s$^{-1}$ for viscosities in the range of 10 to 100.

It is known that the stability of pilocarpine decreases when the pH approaches neutral. At a pH of 6 or over, pilocarpine is stable only for a few weeks, or even a few days. However, by lowering the pH below 6 the degradation of pilocarpine is reduced markedly and it is sufficiently stable for commercial purposes.

However, when the pH is lowered the bioavailability of the active agents are reduced compared to almost neutral solutions. According to the invention, the reduction in bioavailablity is compensated for by increasing the viscosity of the formulation, thus providing for a product allowing a longer contact time on the eye surface.

The agents to be used according to the invention in combination with pilocarpine for the treatment of ocular hypertension are generally speaking carbonic anhydrase inhibitors, prostaglandins or any agent known in the art for blocking or activating the adrenergic receptors, such as β-blocking agents, of which typical examples are carteolol, befunolol, metipronalol, pindolol, betaxolol, levobutanol and especially timolol, and their ophthalmologically acceptable salts and prodrugs.

The ophthalmologically acceptable carrier vehicle is advantageously water, or a mixture of water and an ophthalmologically acceptable organic solvent, which as such are known in the art. The preparation according to the invention may also contain further ophthalmologically acceptable adjuvants.

In order to regulate or stabilize the pH, conventional pH-regulating agents such as acids or bases may be used, or suitable buffers, such as phosphate buffer, borate buffer, acetate buffer, or citrate buffer. To regulate the tonicity of the product, substances conventionally used for this purpose may be used, such as sodium chloride, potassium chloride, glycerol, mannitol, sorbitol, sodium borate, sodium acetate or the like.

The viscosity is adjusted by using, in the formulation, a suitable viscosity enhancing agent in an amount to give the desired viscosity level. Typical examples are the cellulose derivatives, such as hydroxypropyl methylcellulose (HPMC; e.g. Methocel by Colorcon, UK), sodium carboxymethylcellulose (e.g. Blanose by Aqualon, UK), methylcellulose (e.g. Methocel A by Colorcon UK), polyvinylpyrrolidone (e.g. Plasdone by GAF, UK), polyvinylalcohols (e.g. Polyviol by Wacker Chemicals UK), dextrans (e.g. Dextran by Sigma, USA), polyacrylic acids (e.g. Carbopol by Goodrich, UK) etc. The amount of polymer to be added depends in addition to the desired viscosity level, also on the polymer used, and can be easily determined by a person skilled in the art. In addition to raising the viscosity of the formulation, the use of the said polymers may have additional advantages such as a lubricating effect on the eye, as well as a stabilizing effect on the tear film, which are beneficial effects for patients suffering e.g. from dry eyes.

In case an antimicrobial agent is necessary, as is the case when packaging the preparation in multi-dose-containers, but not when packaging the same in unit-dose-containers, agents known for this purpose may be used, such as quaternary ammonium compounds, e.g. benzalkonium chloride, benzyl alcohol, mercury salts, thiomersal, chlorhexidine, chlorobutanol or the like, as such or in combination.

An advantageous eye drop formulation according to the invention is made in sterile water as the carrier vehicle and has the following composition (% w/v): pilocarpine HCl 1–5%, preferably 2–4%, in combination with a β-blocker, especially timolol, in an amount of 0.1–1%, preferably 0.25–0.5%, HPMC as the viscosity enhancer in an amount of 0.3 to 1% to give a viscosity of 10 to 150 mPas, preferably 15 to 50 mPas, and citrate buffer to give a pH of 4.5–5.5. In addition the formulation may contain an acceptable microbial preservative, such as benzalkonium chloride, typically in an amount of 0.04–0.2 mg/ml.

The invention also concerns a process for the preparation of an eye drop formulation as defined, which comprises combining pilocarpine and a further agent for the treatment of ocular hypertension with an ophthalmologically acceptable carrier, adjusting the pH to a value of 3.5 to 5.8 and the viscosity to a value of 10 to 25000 mPas, and possibly adding further ophthalmologically acceptable adjuvants.

The invention also concerns the use of the eye drop formulation for the treatment of ocular hypertension and glaucoma.

The invention is illustrated with the following examples without limiting the same.

EXAMPLE 1

Multi-Dose Formulation

| Composition (mg) | A | B |
| --- | --- | --- |
| Pilocarpine HCl | 20.0 | 40.0 |
| Timolol maleate | 6.84 | 6.84 |
| Citric acid monohydr. | 1.12 | 0.88 |
| Sodium citrate dihydr | 5.79 | 6.13 |
| Benzalkon. chlorid | 0.1 | 0.1 |
| HPMC | 5.0 | 5.0 |
| Sterile water ad | 1.0 ml | 1.0 ml |

The eye drop solution according to this example is made in three stages. In the first step the hydroxypropyl methylcellulose is stirred in sterile water. The solution is sterilized in an autoclave. The autoclaved solution is cooled to room temperature while stirring.

In the second step the benzalkonium chloride, citric acid, sodium citrate, pilocarpine hydrochloride and the timolol maleate are dissolved in sterile water at room temperature. The solution is sterilized by filtration on filter with a pore size of 0.2 μm.

In the third and last step the solutions prepared in the two steps above are combined aseptically and mixed until they form homogenous solution. The pH of the solution obtained is 5.3 and its viscosity 25 mPas. The solution is packed in traditional eye drop bottles.

EXAMPLE 2

Unit-Dose Formulation

| Composition (mg) | A | B |
| --- | --- | --- |
| Pilocarpine HCl | 20.0 | 40.0 |
| Timolol maleate | 6.84 | 6.84 |
| Citric acid monohydr. | 1.12 | 0.88 |
| Sodium citrate dihydr. | 5.79 | 6.13 |
| HPMC | 5.0 | 5.0 |
| Sterile water ad | 1.0 ml | 1.0 ml |

The solutions are prepared according to the Example 1. The pH or the solution obtained is 5.3 and the viscosity 25 mPas. The solution is packed in unit-dose-containers.

EXAMPLE 3

Unit-Dose-Formulation

| Composition (mg) | |
| --- | --- |
| Pilocarpine HCl | 20.0 |
| Timolol hemihydr. | 5.12 |
| Citric acid monohydr. | 2.40 |
| Sodium citrate dihydr. | 4.00 |
| HPMC | 5.0 |
| Sterile water ad | 1.0 ml |

The solution is prepared according to the Example 1. The pH or the solution obtained is 5.3 and the viscosity 25 mPas. The solution is packed in unit-dose-containers. By adding to the formulation benzalkonium chloride 0.10 mg/ml, a corresponding multi-dose formulation is obtained.

EXAMPLE 4

| Composition (mg) | |
| --- | --- |
| Pilocarpine HCl | 20.0 |
| Timolol maleate | 6.84 |
| Citric acid monohydr. | 1.12 |
| Sodium citrate dihydr. | 5.79 |
| Benzalkon. chloride | 0.10 |
| Polyvinylalcohol 115000 | 40.00 |
| Sterile water ad | 1.0 ml |

The solution is prepared according to the Example 1. The pH of the solution obtained is 5.3 and the viscosity 35 mPas.

EXAMPLE 5

| Composition (mg) | |
| --- | --- |
| Pilocarpine HCl | 20.0 mg |
| Betaxolol HCl | 5.6 mg |
| HPMC | 5.0 mg |
| NaOH/HCl ad | pH 5.3 |
| Sterile water ad | 1.0 ml |

The solution is prepared according to the Example 1. The pH of the solution obtained is 5.3 and the viscosity 25 mPas.

EXAMPLE 6

In the following the preparation of two high-viscosity products is described.

| Composition (mg) | |
| --- | --- |
| Pilocarpine HCl | 20.0 |
| Timolol maleate | 6.84 |
| Citric acid monohydr. | 1.12 |
| Sodium citrate dihydr. | 5.79 |
| Benzalkon. chloride | 0.10 |
| Carbopol ® 941 | 9.0 |
| Natr. hydr. q.s. ad | pH 5.0—5.5 |
| Sterile water ad | 1.0 g |

The solution is prepared according to the Example 1. The pH of the solution obtained is 5.2 and the viscosity 24000 mPas.

| | |
|---|---|
| Pilocarpine HCl | 20.0 |
| Timolol hemihydr. | 5.12 |
| Citric acid monohydr. | 1.12 |
| Sodium citrate dihydr. | 5.79 |
| Benzalkon. chloride | 0.10 |
| Carbopol ® 941 | 7.5 |
| Natr. hydr. q.s. ad | pH 5.0–5.5 |
| Sterile water ad | 1.0 g |

The solution is prepared according to the Example 1. The pH of the solution obtained is 5.5 and the viscosity 13700 mPas.

It is claimed:

1. Eye drop formulation, which, in combination, comprises a single polymer, pilocarpine, a β-blocking agent and an ophthalmologically acceptable carrier wherein the pH of the formulation is from 3.5 to 5.8 and the viscosity is from 10 to 25000 mPas.

2. Formulation according to claim 1 wherein the pH is from 4.5 to 5.5.

3. Formulation according to claims 1 or 2 wherein the viscosity of the formulation is from 10 to 150 mPas.

4. Formulation according to claim 1 wherein the pH is adjusted with a suitable buffer.

5. Formulation according to claim 1 wherein the carrier is hydroxypropyl methylcellulose.

6. Formulation according to claim 1 wherein the concentration of β-blocking agent is from 0.1 to 1% (w/v), and that of pilocarpine from 1 to 5% (w/v).

7. Formulation according to claim 1 wherein the β-blocking agent is a timolol compound.

8. Formulation according to claim 1 wherein the formulation is in unit dose form.

9. Process for the preparation of an eye drop formulation according to claim 1 comprising combining pilocarpine and a β-blocking agent and an ophthalmologically acceptable carrier, adjusting the pH to a value of 3.5 to 5.8 and the viscosity to a value of 10 to 2500 mPas.

10. In a method for treating an eye with a mixture of pilocarpine and a beta-blocking agent, the improvement comprising:

forming the pilocarpine and the beta-blocking agent into an aqueous solution containing a single polymer deliverable to the eye as a drop;

adjusting the pH of the solution to a value of 3.5 to 5.8 such that the pilocarpine is stable against degradation for more than a few days in the solution and adjusting the viscosity of the solution to a value of 10 to 25000 mPas;

storing the solution in a sealed container; and delivering the stored solution in drop form to the surface of the eye wherein the viscosity of the solution substantially increases the bioavailablility of the beta-blocking agent upon delivery to the eye.

11. A method for treating an eye with a composition containing pilocarpine and a beta-blocking agent comprising:

forming an aqueous solution containing a single polymer the pilocarpine and the beta-blocking agent;

adjusting the pH of the solution to a value of 3.5 to 5.8 such that the pilocarpine is stable against degradation in the solution upon storage in a container and adjusting the viscosity of the solution to a value of 10 to 25000 mPas;

storing the solution in a sealed container, and delivering the stored solution to the surface of the eye wherein the viscosity of the solution substantially increases the bioavailability of the beta-blocking agent upon delivery to the eye.

* * * * *